(12) United States Patent
Sullivan et al.

(10) Patent No.: US 7,957,799 B2
(45) Date of Patent: Jun. 7, 2011

(54) NON-INVASIVE CARDIAC POTENTIATION THERAPY

(75) Inventors: Joseph L. Sullivan, Kirkland, WA (US); Fred W. Chapman, Renton, WA (US); Robert G. Walker, Bothell, WA (US); William J. Havel, Maple Grove, MN (US); D. Curtis Deno, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 861 days.

(21) Appl. No.: 11/742,063

(22) Filed: Apr. 30, 2007

(65) Prior Publication Data

US 2008/0269818 A1    Oct. 30, 2008

(51) Int. Cl.
*A61N 1/39* (2006.01)

(52) U.S. Cl. ............. 607/5; 607/2; 607/3; 607/4; 607/6; 607/7; 607/23; 607/24; 607/25; 607/26; 607/27

(58) Field of Classification Search .................. 607/2–7, 607/23–27
See application file for complete search history.

(56) References Cited

U.S. PATENT DOCUMENTS

| | | | |
|---|---|---|---|
| 5,213,098 A | 5/1993 | Bennett et al. | |
| 6,314,319 B1 | 11/2001 | Kroll et al. | |
| 6,438,408 B1 | 8/2002 | Mulligan et al. | |
| 6,738,667 B2 | 5/2004 | Deno et al. | |
| 2003/0074029 A1* | 4/2003 | Deno et al. | 607/23 |
| 2003/0233129 A1* | 12/2003 | Matos | 607/5 |
| 2004/0022063 A1 | 2/2004 | Le Bars et al. | |
| 2004/0049235 A1 | 3/2004 | Deno et al. | |
| 2004/0215271 A1* | 10/2004 | Sullivan | 607/27 |
| 2005/0075673 A1 | 4/2005 | Warkentin et al. | |
| 2005/0075674 A1 | 4/2005 | Zillmer et al. | |
| 2005/0075676 A1 | 4/2005 | Deno et al. | |
| 2005/0090871 A1 | 4/2005 | Cho et al. | |
| 2005/0090872 A1 | 4/2005 | Deno et al. | |
| 2006/0142809 A1 | 6/2006 | Kroll et al. | |
| 2006/0149184 A1 | 7/2006 | Soykan et al. | |
| 2006/0247698 A1 | 11/2006 | Burnes et al. | |

* cited by examiner

*Primary Examiner* — Niketa I Patel
*Assistant Examiner* — Rex Holmes
(74) *Attorney, Agent, or Firm* — Stephen W. Bauer; Reed A. Duthler

(57) ABSTRACT

An external cardiac medical device for delivering Cardiac Potentiation Therapy (CPT). Techniques used with the device include initial diagnosis of the patient, delivery of the CPT, and configuration of the external device, so that CPT can be effectively and efficiently provided. In particular, these techniques include initially determining whether a patient should receive CPT, how to set the coupling interval for delivering CPT, how to configure the external medical device to deliver CPT stimulation pulses while not adversely affecting the device's ability to sense a patient's cardiac parameters and/or signals.

14 Claims, 5 Drawing Sheets

NON-INVASIVE CARDIAC POTENTIATION THERAPY

BACKGROUND

The present invention generally relates to cardiac external medical devices.

A treatment known as Cardiac Potentiation Therapy (CPT) can be used to increase a person's cardiac output by electrically stimulating one or more heart chambers to induce post-extrasystolic potentiation. This therapy is used to improve hemodynamic function for a patient that has lost function due to myocardial infarction. In brief, CPT works by increasing the intracellular calcium in cardiomyocytes, thereby increasing the force of myocardial contraction in response to stimulation. Such benefit is achieved when the electrical stimulus is delivered to the heart near the end of the refractory period of the cardiac cycle. Generally, the electrical stimulus delivered does not induce a cardiac contraction, but rather facilitates calcium transport into the cell, which, in turn, increases the strength of a subsequent contraction. In this way, CPT increases the patient's ejection fraction, which, in turn, increases cardiac output.

As is known, proper application of CPT requires knowledge of the cardiac refractory period. A stimulus provided before the end of the refractory period has been found to not induce a cardiac action potential and tends to not affect contractile force. Conversely, a stimulus provided too long after the end of the refractory period tends to have a reduced benefit. In the extreme, for example, if the stimulus is provided at the regular R-R interval, no effect is generally realized.

Some conventional methods used for determining the end of the refractory period have involved using one or more signals stemming from inside the body. For example, an intracardiac electrocardiogram (ECG) signal can be used to determine the end of the refractory period by adjusting the application of the electrical stimulus, or rather, the potentiation pulse. If the potentiation pulse produces a cardiac action potential, then such pulse is known to be outside the refractory period. Conversely, if no action potential is produced following delivery of the potentiation pulse, then such pulse is known to be inside the refractory period. The refractory period duration doesn't change very much on a beat-to-beat basis. As such, a "hunting" algorithm can be employed, for example, to continually adjust the location of the potentiation pulse, e.g., relative to the R wave.

Invasive blood pressure waveforms can alternatively be used in adjusting the location of the potentiation pulse. For example, an optimal location of the potentiation pulse is the location that produces the maximum diastolic blood pressure on the next subsequent beat. Therefore, if a hunting algorithm is employed, the best relative location of the potentiation pulse can be determined by measuring the diastolic blood pressure over a series of cardiac cycles.

To date, implantable cardiac medical devices have generally been used in providing CPT to patients. Some examples of implantable cardiac medical devices include hemodynamic monitors (IHMs), cardioverter-defibrillators (ICDs), cardiac pacemakers, cardiac resynchronization therapy (CRT) pacing devices, and drug delivery devices. Implantable devices have generally been viewed as ideal systems for administering CPT to patients due to a number of reasons. First, the devices are already configured for internally monitoring the hemodynamics of a patient, e.g., via sensors from the implantable devices. As such, the hemodynamic information gathered is generally quite precise. As a result, providing CPT to a patient based on such information is both effective and efficient. Second, many implantable devices are already equipped to deliver electrical stimulus to the patient when the need arises. Therefore, these devices can further be used to deliver CPT, as described above, via programming of the devices.

It is well known that patients not having implantable medical devices can be just as susceptible to reduced cardiac output episodes as those patients having such devices. In turn, such patients would equally benefit from CPT; however, the patients would only have access to CPT through external cardiac medical devices. For example, patients suffering from Pulseless Electrical Activity (PEA) may not be implanted with cardiac medical devices. As is known, PEA is a condition that involves a reduced (or nonexistent) cardiac output, whereby a person in PEA has an organized electrical cardiac rhythm but little or no blood flow. PEA can commonly occur for a period of time after a patient has been given defibrillation shocks from an external cardiac medical device. For example, in "successful" defibrillations, where patients regain an electrical pulse as demonstrated by an ECG, approximately 50% of the patients will not exhibit a physical pulse as demonstrated by restored, peripherally measured, blood pressure. In such cases, CPT could be used to help restore normal cardiac output during the recovery period of the patient. As is known, PEA is also found to occur at other times as well. Currently, the effects of therapy are limited in treating PEA; however, as alluded to above, CPT may be beneficial.

Unfortunately, no external cardiac medical devices are commercially available which have been configured to provide CPT. One reason for this could be that implementation of CPT with respect to external devices presents a number of challenges not currently faced with implantable devices. For example, as known from CPT-equipped implantable devices, effective administration of CPT depends greatly on accurate monitoring of a patient's cardiac signals and/or hemodynamics; however, such accurate monitoring can be problematic for external devices. For instance, ECG signals measured externally can be difficult to monitor because noise from the external stimulation pulse often obscures the cardiac action potential.

Another reason for the lack of CPT-equipped external devices may be that the design of implantable devices with CPT functionality is still fairly new. As such, the implementation of CPT with implantable devices may be indirectly delaying implementation of CPT with external devices. A further reason may be that testing the populations of patients requiring CPT when using external devices has proved to be more difficult in comparison to testing patients with implantable devices, from which information can simply be downloaded and studied.

What are needed are apparatus and systematic methods to address or overcome one or more of the challenges briefly described above with respect to external cardiac medical devices.

DETAILED DESCRIPTION

Figure 1:
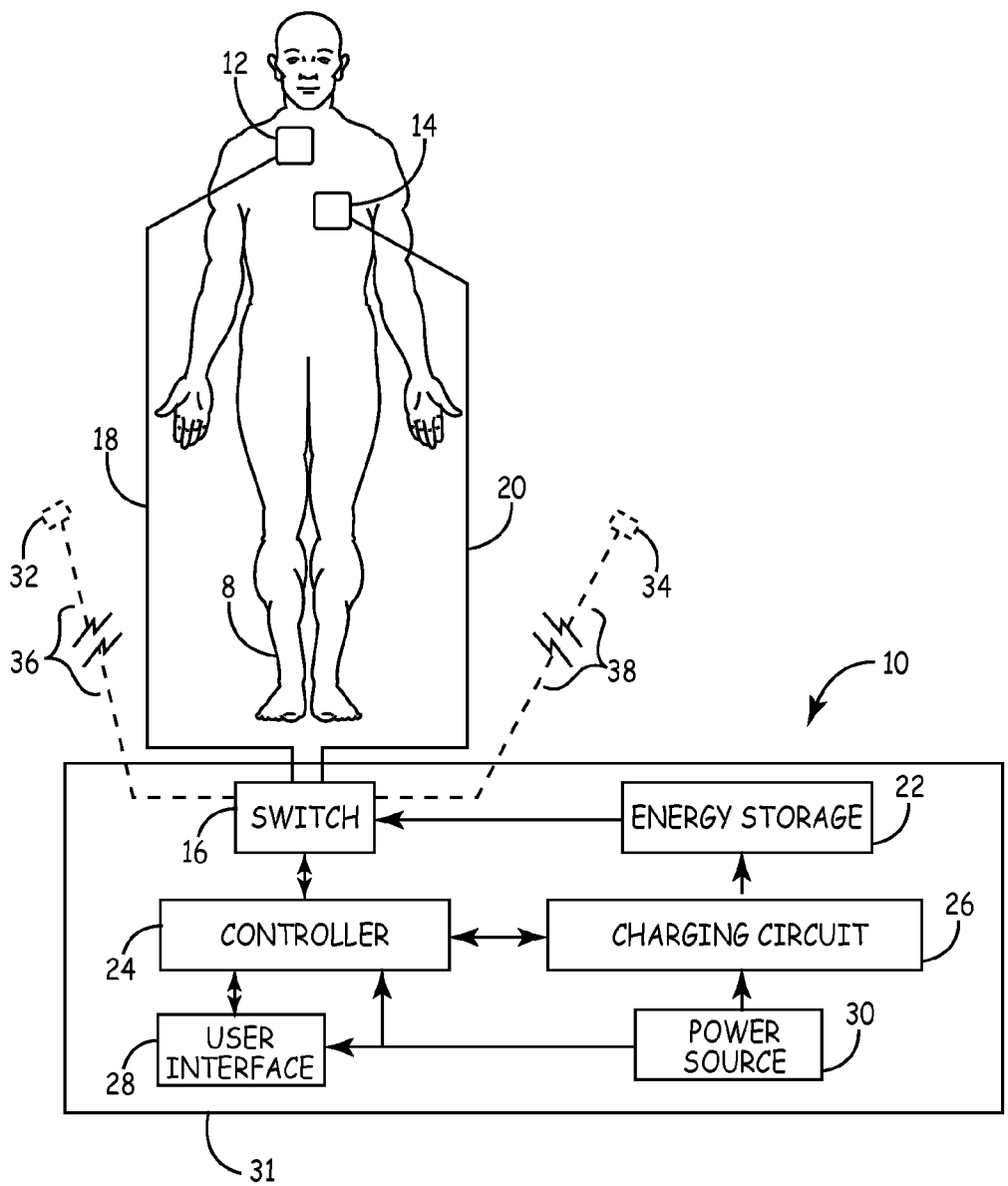
FIG. 1 is block diagram illustrating an external cardiac medical device that can be used in accordance with certain embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims. In addition, it should be appreciated that the techniques and methods described and illustrated herein can be implemented within a medical device in a variety of manners. For example, in certain embodiments, instructions corresponding to one or more of the techniques and methods are programmed within a controller (e.g., a processor) within such medical device. One skilled in the art would be familiar with such programming practices as well as other typical manners of implementation within medical devices. In turn, such manners of implementation are not discussed in further detail herein.

As described above, Cardiac Potentiation Therapy (CPT) is generally used to increase cardiac output. As described above, CPT stimulations improve the pumping efficiency of the patient's heart by inducing post-extrasystolic potentiation, which involves management of the distribution of calcium ions that contribute to contraction of cardiac myocytes. More detailed discussion regarding CPT as well as its functioning and therapeutic benefits can be found in U.S. Patent Application Pub. No. US 2006/0149184, the disclosure of which is incorporated by reference herein in relevant part.

Unfortunately, as described above, CPT has not been available to patients being treated with an external cardiac medical device (e.g., external pacemaker, external defibrillator, etc.). As such, embodiments of the invention involve optimal methods of providing CPT using an external cardiac medical device. The embodiments involve a variety of techniques, for example, related to initial diagnosis of the patient, delivery of the CPT, and configuration of the external device, so that CPT can be effectively and efficiently provided. In particular, these techniques include initially determining whether a patient should receive CPT, how to set the coupling interval for delivering CPT, how to configure the external medical device to deliver CPT stimulation pulses while not adversely affecting the device's ability to sense a patient's cardiac parameters and/or signals, as well as other aspects that are especially applicable to external devices and the administration of CPT.

While the above-mentioned techniques are collectively described herein, it should be appreciated that they can be used individually or in any combination with respect to their implementation in external devices. In addition, while apparatus and techniques are embodied herein with respect to external defibrillators, it is to be appreciated that the invention should not be so limited. In general, the apparatus and techniques can be applicable to any external cardiac medical device configured to (i) non-invasively monitor hemodynamic parameters and/or other cardiac signals of a patient and (ii) deliver electrical stimulus to the patient.

Further, while the embodiments herein involve treating a patient in cardiac arrest, whereby CPT is administered to the patient upon the onset of PEA, it should be appreciated that the described apparatus and techniques can be further applicable to any patient experiencing cardiac output deficiencies. For example, patients suffering from heart failure could benefit from CPT. As is known, heart failure is a degenerative condition that affects the lives of millions of people. The condition is characterized by a reduced cardiac output and a decreased work capacity for the person. Drugs can be beneficial in reducing the symptoms of heart failure, but they generally slow, rather than stop, the progress of the disease. Therefore, CPT could be used to treat the reduced cardiac output brought on by heart failure. In addition, patients who are asystolic or bradycardia with a low cardiac output could benefit from CPT. In such cases where CPT is used, a double stimulus can be provided—one electrical stimulus to trigger a cardiac action potential and a second for potentiation. As described above, the potentiation pulse is best applied near the end of the refractory period.

FIG. 1 is a block diagram showing a patient 8 coupled to an external medical device that may be used in accordance with certain embodiments of the invention. As shown, the external medical device can involve a defibrillator 10. In certain embodiments, the defibrillator 10 can involve an automated external defibrillator (AED); however, in other embodiments, the defibrillator 10 could just as well involve a manual external defibrillator. The defibrillator 10 can be used to administer defibrillation shocks to the patient 8 via electrodes 12 and 14, which may be hand-held electrode paddles or adhesive electrode pads placed on the skin of the patient 8. The body of the patient 8 provides an electrical path between the electrodes 12 and 14. In certain embodiments, the electrodes 12, 14 are also used for sensing cardiac information of the patient 8 via sensors (e.g., operatively associated with one or more of the electrodes 12, 14).

Generally, the electrodes 12 and 14 are coupled to a switch 16 via conductors 18 and 20. In certain embodiments, the electrodes 12 and 14 are replaceable. The switch 16 couples the electrodes 12 and 14 to the output of an energy storage device 22. The switch 16 is of conventional design and can be formed, for example, of electrically operated relays. Alternatively, the switch 16 can involve an arrangement of solid-state devices such as silicon-controlled rectifiers or insulated gate bipolar transistors. In each case, the switch 16 is capable of carrying relatively high currents from the energy storage device 22 to the electrodes 12, 14.

The energy storage device 22 includes components, such as one or more capacitors, that store energy to be delivered to the patient 8 via the electrodes 12, 14. Before a defibrillation pulse may be delivered to the patient 8, the energy storage device 22 needs to be charged. A controller 24 (e.g., a microprocessor) directs a charging circuit 26 to charge the energy storage device 22 to a high voltage level. The charging circuit 26 includes, for example, a flyback charger that transfers energy from a power source 30 to the energy storage device 22. Because the life of the patient 8 may depend upon receiving defibrillation, charging is generally rapid so that the defibrillation shock may be delivered with little delay.

When the energy stored in the energy storage device 22 reaches the desired level, the defibrillator 10 is ready to deliver the defibrillation shocks. The shocks may be delivered automatically or manually, depending on whether the defibrillator 10 is an AED or a manual external defibrillator.

For example, when the shocks are delivered automatically, the controller 24 activates one or more input/output (I/O) devices (e.g., such as an indicator light and/or a voice prompt) generally included on a user interface 28, which warn the operator that the defibrillator 10 is ready to deliver defibrillation shocks to the patient 8. This warning informs the operator of the impending shocks so that no one other than the patient 8 will receive the defibrillation shocks. The controller 24 then activates the switch 16 to electrically connect the energy storage device 22 to the electrodes 12 and 14, and thereby delivers defibrillation shocks to the patient 8. Conversely, in the case of manual delivery, the controller 24 may activate one or more of the I/O devices on the user interface 28, which informs the operator that the defibrillator 10 is ready to deliver defibrillation shocks to the patient 8. In turn, the operator can activate the switch 16 and thereby deliver the defibrillation shocks to the patient 8.

An external cardiac medical device, such as the defibrillator 10 described above and illustrated in FIG. 1, is often employed to treat a patient in cardiac arrest. Cardiac arrest may be the result of one or more heart conditions that the patient suffers from, or conversely, may have been brought on by a stressful episode. Ventricular Fibrillation (VF) is the most common electrical mechanism in cardiac arrest, and is responsible for most cardiac arrest occurrences. However, ventricular tachyarrhythmia, severe bradyarrhythmias, PEA, and asystole have also been found to be responsible for cardiac arrest occurrences as well. Regardless, upon finding a patient in cardiac arrest, time is of the essence in restoring the patient's heart to a normal sinus rhythm.

In certain embodiments, the controller 24 is generally configured to perform functions other than facilitating the defibrillation shocks to the patient 8. One of these functions is monitoring cardiac information, namely one or more hemodynamic parameters and/or cardiac signals of the patient 8, e.g., via sensors (e.g., operatively associated with one or more of the electrodes 12, 14). As should be appreciated, while not shown in FIG. 1, the controller 24 has or is connected to memory (e.g., within housing 31 of the defibrillator 10) so that the cardiac information can be stored, if warranted. To avoid "blind defibrillation", the controller 24 is commonly programmed to interpret the cardiac information prior to delivering (in the case of an AED) or prompting a caregiver to deliver (in the case of a manual external defibrillator) a defibrillation shock to the patient 8. For example, the cardiac information can be electrocardiogram (ECG) signals sensed via the electrodes 12 and 14, whereby the controller 24 would interpret the ECG signals to verify the patient 8 needs defibrillation. Further, in monitoring the cardiac information following defibrillation of the patient, the controller 24 can evaluate the efficacy of the administered defibrillation shocks. For example, ECG signals of the patient 8 can be passed to the controller 24 following defibrillation. In turn, the controller 24 can be used to interpret the ECG information in determining whether the patient 8 has regained an organized electrical cardiac rhythm. Generally, if an organized electrical cardiac rhythm is regained; further defibrillation shocks would not be warranted.

As is known, the goal of defibrillation is to depolarize the heart with electrical current and cause the heart to reestablish a normal sinus rhythm. Such normal sinus rhythm is based on proper organized electrical cardiac rhythm as well as proper cardiac output. Defibrillation shocks administered to the patient 8 via the defibrillator 10 can lead to an organized electrical cardiac rhythm being restored. Proper cardiac output can be found to naturally follow as a result of restoring the organized electrical cardiac rhythm. However, in some cases, proper cardiac output does not follow. In other cases, while the patient's cardiac output may be initially restored, the cardiac output can be found to suddenly drop off after a short time. In both cases, the patient would be in or would enter into a state of PEA, as described above. It has been found that, given proper diagnosis and implementation using an external cardiac medical device, CPT can be used to treat patients in PEA as well as patients experiencing other cardiac output deficiencies. By using CPT, in such cases, the patient's cardiac output can be increased. As a result, in cases involving PEA as described above, normal sinus rhythm for the patient's heart can be achieved, and hopefully, permanently restored.

While it is frequently the case that a patient can suffer from PEA following defibrillation, patients can also be found to suffer from PEA in other cases not involving defibrillation, as mentioned above. As such, PEA, as used herein, can refer to any type of pulseless electrical activity, including post-defibrillation shock PEA, "pseudo" PEA (i.e., wherein a pulsatile increase in pressure in the left ventricle occurs, but does not reach the arteries), true PEA (i.e., a patient found in a state of PEA), and normotensive PEA. While all types of PEA may be treated with the techniques of the present invention, the treatment of post-shock, post-cardioversion or post-defibrillation PEA is one particular object described herein.

Diagnosis of the Patient: Even if an external cardiac medical device, e.g., the defibrillator 10, is adapted with CPT functionality, an initial concern involves how the device would determine whether the patient would benefit from CPT. In particular, what criteria can be used by the external device, e.g., the defibrillator 10, in making an effective determination as to whether the patient 8 needs CPT?

If the patient 8 is in cardiac arrest, it is generally not easy to determine whether CPT would be warranted. However, it should be appreciated that this would be a secondary consideration to immediately treating the patient 8. For example, using an external defibrillator, such as the defibrillator 10 of FIG. 1, the primary treatment for a cardiac arrest patient in VF involves delivery of a defibrillation shock to restore normal sinus rhythm, as described above. Subsequently, the controller 24 (housed within the defibrillator 10) can be used to monitor/interpret cardiac information of the patient 8, namely one or more hemodynamic parameters and/or cardiac signals of the patient 8, to determine the condition of the patient's heart.

As described above, through such monitoring/interpretation of an ECG signal, controllers in conventional defibrillators have generally been able to determine whether administered defibrillation was successful in restoring organized electrical cardiac rhythm to the patient's heart. As already mentioned, the patient's cardiac output may not naturally come back as a result of the electrical cardiac rhythm being restored. Conventionally, one would use cardiopulmonary resuscitation (CPR) to help maintain and potentially restore normal oxygen and blood flow within the patient. In addition, drugs (e.g., such as epinephrine) can also be administered as an aid to restore the patient's hemodynamics. Alternatively, it has been found that CPT is an effective tool in restoring hemodynamic function of the patient. As can be appreciated, it generally would not be wise to apply CPT to a patient who was generating adequate blood flow spontaneously. As such, in certain embodiments, one or more methods can be used to determine whether the patient should receive CPT. In particular, the methods addressed below are used in determining whether the patient is in PEA; however, as should be appreciated, these methods are also applicable in determining whether the patient has reduced cardiac output functioning, providing the trigger for administering CPT.

As should be appreciated, in determining whether the patient is in PEA via any of the techniques described herein, the external cardiac medical device, such as the defibrillator 10 of FIG. 1, needs to be equipped for implementing such techniques accordingly. In particular, this would involve the controller 24 of the defibrillator 10 being programmed with corresponding instructions. As alluded to above, one skilled in the art would be familiar with such programming practices as well as other typical manners of implementation within medical devices. In turn, such manners of implementation are not discussed in further detail below.

Whether the patient is in PEA following defibrillation can depend, at least in part, on the viability or condition of the patient's heart, i.e., the ability of the heart to function mechanically, or pump blood, provided that an organized electrical rhythm is restored. The heart becomes less viable as time passes in the absence of flow of oxygenated blood to the heart and the heart becomes metabolically deranged. This derangement may include decreased energy stores, increased intracellular calcium, decreased pH, increased extracellular potassium, and/or other anomalies. Accordingly, the viability of the heart can provide an effective indicator as to whether the heart is in PEA, as discussed below.

Accordingly, in certain embodiments, the controller 24 can use the cardiac information (one or more hemodynamic parameters and/or cardiac signals), monitored by the defibrillator 10 (e.g., via the electrodes 12, 14) or obtained by the operator, to determine the current viability, or condition, of the heart. In certain embodiments, the cardiac information, once gathered, is quantified by the controller 24 in making the determination. This quantification can be attained directly from the monitored cardiac information, or alternately, can be attained indirectly by using the cardiac information in calculations. In certain embodiments, multiple techniques of quantification can be used, using different cardiac information or different analysis techniques applied to the same cardiac information or both, and used in combination to determine whether the patient is in PEA. From such quantification, if PEA is found to exist, such would provide an indicator for the defibrillator 10 that the patient can benefit from CPT. As should be appreciated, if the patient is in asystole following defibrillation and remains in asystole thereafter, the quantification of the monitored cardiac information would accordingly show a lack of mechanical cardiac activity and/or electrical cardiac activity (depending on the cardiac information that is monitored). In such case, as alluded to above, the controller 24 would at least determine that there is deficient cardiac output functioning, thereby triggering administration of CPT, as described below. In certain embodiments, if the monitored cardiac information also indicates lack of electrical cardiac activity, the controller 24 can be configured to direct further therapy (e.g., pacing pulses) to the patient.

As shown in FIG. 1 and described above, the controller 24 functions with the I/O devices included on the user interface 28. As shown, the user interface 28 is operatively associated with the controller 24 for providing outputs to, and obtaining inputs from, the operator of the defibrillator 10. For example, the user interface 28 can include a display, e.g., LEDs, LCD, or some combination thereof, for displaying the patient's ECG waveform and for displaying various system and patient parameters, features, instructions, functions, warnings, alerts, commands, etc. for information to or selection by the operator. In addition, the user interface 28 can include various audio output devices, e.g., a speaker, audio or tactile signal generator, etc. for notifying the operator of various system and patient parameters, features, instructions, functions, warnings, alerts, commands, etc. Further, the user interface 28 can include various user input mechanisms, e.g., control and command buttons, touch screens, voice recognition software, keyboard, mouse or pen-based entry devices, etc., for enabling the operator to input various system and patient parameters, instructions, commands, etc.

Accordingly, in the case of the defibrillator 10 being an AED, following defibrillation of the patient 8 and analysis of the patient's cardiac information, the defibrillator 10 can inform the operator of the condition of the patient 8 via one or more of the I/O devices included on the interface 28. For example, the display can be used to indicate that "Patient is in PEA". In turn, the operator will be instructed via one or more of the I/O devices to leave the electrodes 12, 14 in place for administration of CPT to the patient 8. Conversely, in the case of the defibrillator 10 being an external manual defibrillator, again following defibrillation of the patient 8 and analysis of the cardiac information, the defibrillator 10 can inform the operator of the condition of the patient 8, as exemplified above. Further, if the condition of the patient necessitates delivery of CPT, the operator is instructed to activate CPT, e.g., via a flipping of a switch on the defibrillator 10.

There are many methods of assessing the viability of a patient's heart, and in turn, the patient's cardiac output, via cardiac information. One method would simply involve the operator checking the pulse of the patient. In turn, if the defibrillator 10 detects an organized ECG signal but the patient has no pulse, the defibrillator 10 can be used to apply CPT. In the case of an AED, in certain embodiments, the defibrillator 10 (via the controller 24) would prompt the operator to check for a pulse, allow for subsequent operator input (the operator indicating pulse or no pulse via the I/O devices on the user interface 28), then determine whether CPT should be applied based on the operator input along with ECG analysis. Conversely, in the case of a manual external defibrillator, in certain embodiments, CPT can be available as a manually operated feature (in the same manner that external pacing is conventionally applied), involving the above steps with respect to an AED, and requiring the operator to further determine when the CPT should be turned on or off.

Another method of assessing the viability of the patient's heart would be to determine whether the patient has had a sufficiently long "down time". As used here, "down time" refers to duration of VF. It is generally known that patients with a long "down time" (e.g., longer than 2 to 3 minutes) are likely to convert to PEA or asystole after a defibrillation shock. As such, CPT could be applied to these patients without specifically verifying that the patient experienced low blood flow because, statistically speaking, the odds are very much in favor of this being the case. Accordingly, in certain embodiments, the duration of ventricular fibrillation is used in assessing the viability of the patient's heart, and in turn, the patient's cardiac output, to determine whether the patient is in PEA.

Numerous techniques for measuring or estimating the duration of VF are known to those skilled in the art. In one example, the properties of the ECG during VF are used to estimate the duration of VF. See, e.g., C. Brown et al., *Physiologic measurement of the ventricular fibrillation ECG signal: estimating the duration of ventricular fibrillation*, Annals of Emergency Medicine 22, 70-74 (1993). In another example, the duration of VF is based on the time interval beginning from when the external cardiac medical device is energized (i.e., turned on) and ending when defibrillation is administered to the patient. In these examples, if the properties of the ECG during VF indicated a long "down time" or the time interval exceeded a specified long "down time" period (e.g., period being pre-programmed within the controller 24 of the defibrillator 10), the device would be triggered to provide CPT. Such triggering would either be automatic in the case of an AED or via a switching on of the CPT functionality from an action of the operator in the case of a manual external defibrillator. In either case, administration of CPT would follow the defibrillation therapy being administered to the patient.

As is known, the viability of a heart in VF for a relatively long period may also depend on other factors, e.g., a patient who has been in ventricular fibrillation for several minutes but who has received effective CPR for some duration may have a more viable heart, and consequently, a lower likelihood of developing PEA than a patient whose heart has not received any oxygenated blood during the period of fibrillation. Thus, in some cases, it may be desirable to use other cardiac information or different analysis techniques in combination with the duration of VF characteristic in deciding whether or not to deliver CPT.

Accordingly, physiologic measurements may be used alone or in combination with said VF duration characteristic to determine the viability of the heart, and in turn, whether the heart is in PEA, thereby serving as a trigger for CPT. Any measurements that can be taken non-invasively and are known to change systematically as the metabolic state of the body deteriorates in the absence of circulation may be applicable. Consequently, such measurements can include optical sensing of blood flow, acoustic sensing of heart sounds, impedance-based sensing, sensing based on a pressure transducer, and accelerometer sensing. For example, measurements can include but are not limited to ECG or EEG (electroencephalogram) or transchest electrical impedance signals, patient temperature, non-invasive blood pressure (NIBP), heart motion measures during VF, heart chamber volume measures, capnography (measure of $CO_2$ in exhaled gases), and pulse oximetry (measure of the oxygenation of the patient's blood). The techniques by which the above measurements are attained non-invasively are generally known to one skilled in the art, and as such, are not covered herein; however, with respect to certain techniques, further description is provided below.

For example, with respect to parameters measured from ECG signals, a succession of wide QRS complexes has been found to be an accurate indicator of a patient not having a pulse. Conversely, a succession of narrow QRS complexes has been found to be an accurate indicator of a patient having a pulse. Accordingly, in certain embodiments, the defibrillator 10 via the controller 24 can start or advise starting CPT in patients with wide QRS complexes, or use a combination of wide QRS complexes and another physiologic measurement (which also indicates patient pulselessness) as a trigger to start or advise starting CPT.

With respect to NIBP techniques, it is well known that both an ECG signal and a NIBP reading (e.g., provided via a blood pressure cuff) can provide adequate information to show that PEA exists, serving as a trigger for administering CPT to the patient. External defibrillators can be equipped to make NIBP readings, and it is possible to incorporate such NIBP functionality into an AED. The concern is with the operator using the defibrillator 10, and whether the operator is medically trained, such as a clinician, so as to know how to take NIBP readings. If the operator is medically trained, the operator, following measurement of the patient's blood pressure, can enter such information via the user interface 28. In turn, the defibrillator 10 can determine whether the patient 8 is in PEA. Conversely, operators that are not medically trained would likely not have the ability to measure the blood pressure of the patient 8. Such untrained operators would generally be working with AEDs. In such cases, the AEDs (via the controller 24 therein) can employ an automatic algorithm that takes an NIBP reading (e.g., from a blood pressure cuff attached to the patient 8 by the operator) and analyzes the reading in combination with the patient's ECG to determine whether the patient is in PEA.

Figure 2:
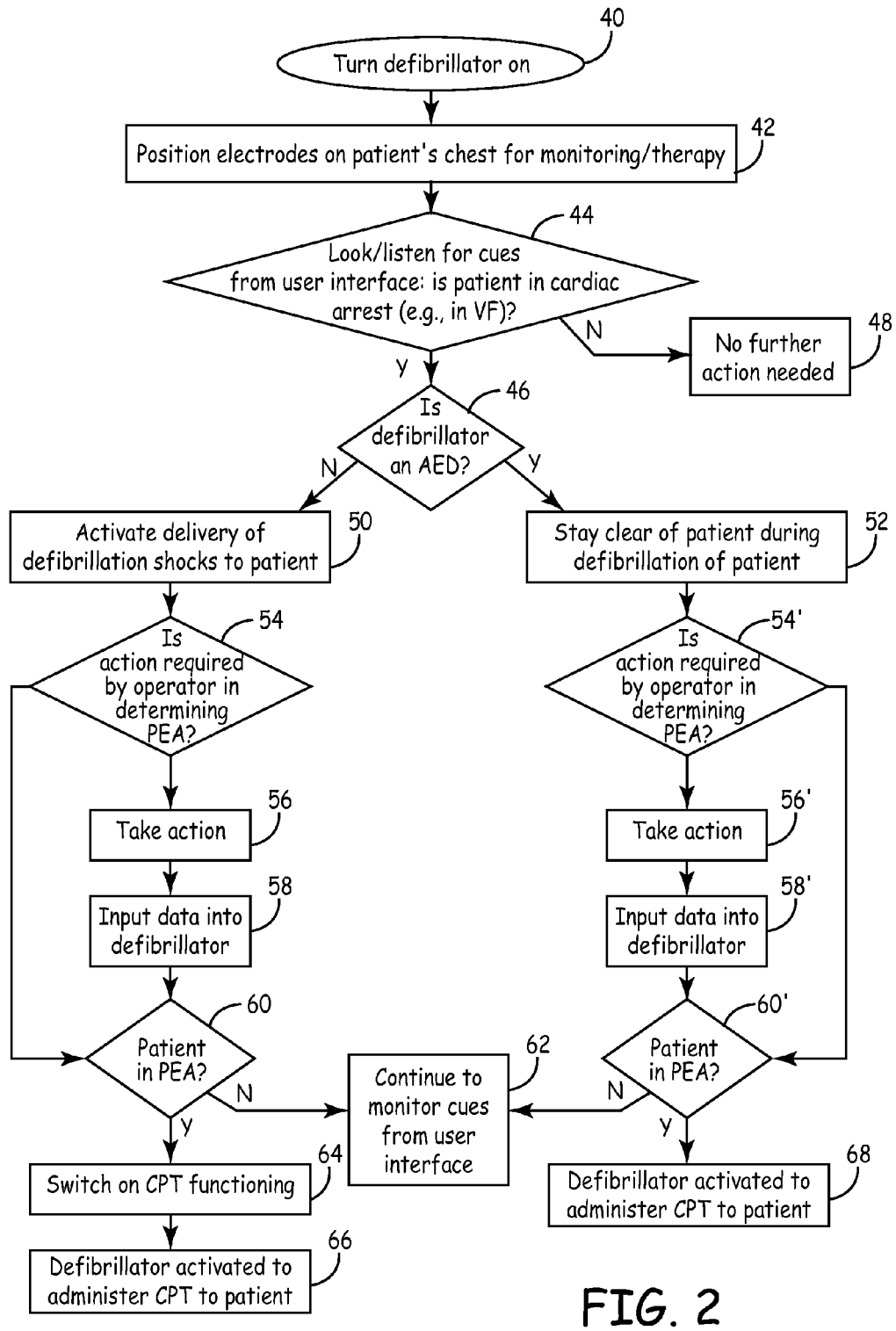
FIG. 2 is a flowchart depicting steps used in addressing diagnosis of a patient with respect to PEA and initial delivery of CPT, if warranted, using the external cardiac medical device of FIG. 1 in accordance with certain embodiments of the invention.

FIG. 2, with reference to the patient 8 and the defibrillator 10 of FIG. 1, is a flowchart depicting steps used in addressing diagnosis of the patient with respect to PEA and initial delivery of CPT, if warranted, in accordance with certain embodiments of the invention. As shown, steps 40 (defibrillator turned on) and 42 (placing electrodes 12, 14 on patient's chest) involve readying the defibrillator 10 for use on the patient 8. Subsequently, step 44 would involve the operator looking/listening for cues from the user interface 28 of the defibrillator 10 for indication as to whether the patient 8 is in a defibrillating form of cardiac arrest (e.g., VF). If the defibrillator 10 indicates that the patient 8 is in such state, depending on whether the defibrillator 10 is a manual external defibrillator or an AED (shown in step 46), the operator would either activate the administration of the defibrillation shocks while staying out of contact with the patient 8 (if the defibrillator 10 is a manual external defibrillator) in step 50 or simply stay out of contact with the patient 8 (if the defibrillator 10 is an AED) while defibrillation shocks are administered by the defibrillator in step 52. If the patient 8 is found to not be in cardiac arrest, no further action is required by the operator, as shown by step 48.

The next series of steps following steps 50 or 52, regardless of whether the defibrillator 10 was a manual external defibrillator or an AED, would be the same. These steps would conclude with the defibrillator 10 (via the controller 24) determining whether the patient 8 is in PEA, so as to necessitate the delivery of CPT. As described above, in some embodiments, the defibrillator 10 may need input from the operator in making this determination, as contemplated in steps 54 and 54'. For example, this may be the case when the operator needs to check the patient 8 for a pulse or needs to check the patient's blood pressure non-invasively, as described above. As described above, these actions would generally be performed by a trained operator, and would occur in steps 56 and 56'. Subsequently, the cardiac information attained by the operator would be relayed to the defibrillator 10 via one or more of the I/O devices on the user interface 28, as shown in steps 58 and 58'. From this information and any other cardiac information gathered by the defibrillator 10, the defibrillator 10 would in turn be able to determine whether the patient is in PEA and would generally indicate such to the operator in steps 60 and 60'. As should be appreciated, if the defibrillator 10 did not solicit input from the operator in steps 54 or 54' in order to make this determination, the flowchart would skip steps 56, 58 or 56', 58', respectively, and go directly to steps 60 and 60', respectively. For example, this may be the case when the existence of PEA is based on VF duration or physiological measurements not requiring input from the operator, as described above.

Upon a determination by the defibrillator 10 that the patient is not in PEA in steps 60 and 60', respectively, the operator, in step 62, would be instructed to continue to monitor the user interface 28 for further instructions. While not shown, such further instructions may involve directing the operator to leave the electrodes 12, 14 in place for certain duration as the patient may need further defibrillation or the need for CPT may arise in a short time. If the defibrillator 10 is a manual external defibrillator and a determination is made that the patient is in PEA, the operator will be prompted to switch on CPT functioning of the defibrillator 10. Upon such switching by the operator in step 64, the defibrillator will be activated for administration of CPT to the patient 8 as shown in step 66. Conversely, if the defibrillator 10 is an AED and a determination is made that the patient is in PEA, the AED will automatically switch on CPT functioning, whereupon the defibrillator is activated for administration of CPT to the patient 8 as shown in step 68.

As described herein, it is often desirable to make an initial assessment of the patient's cardiac condition so as to confirm the patient's need for CPT prior to administering such therapy. Such initial assessment, as described above, can include using the patient's cardiac information as a basis. In the alternative, one could quickly interview people already at the scene to make such an assessment. However, it should be appreciated that it may be just as desirable to administer CPT without making such an assessment. For example, the American Heart Association (AHA) has generally recommended that CPR be administered, at least initially, to a cardiac arrest patient who has been treated with defibrillation shocks, regardless of the patient's ensuing cardiac condition. As such, in certain embodiments, the defibrillator 10 can be configured to trigger CPT, either automatically (in the case of an AED) or via operator actuation (in the case of a manual external defibrillator) after delivery of defibrillation shocks. In turn, CPT is applied for a length of time, after which, CPT is stopped and the cardiac information of the patient is checked to determine whether CPT needs to be continued.

Figure 2A:
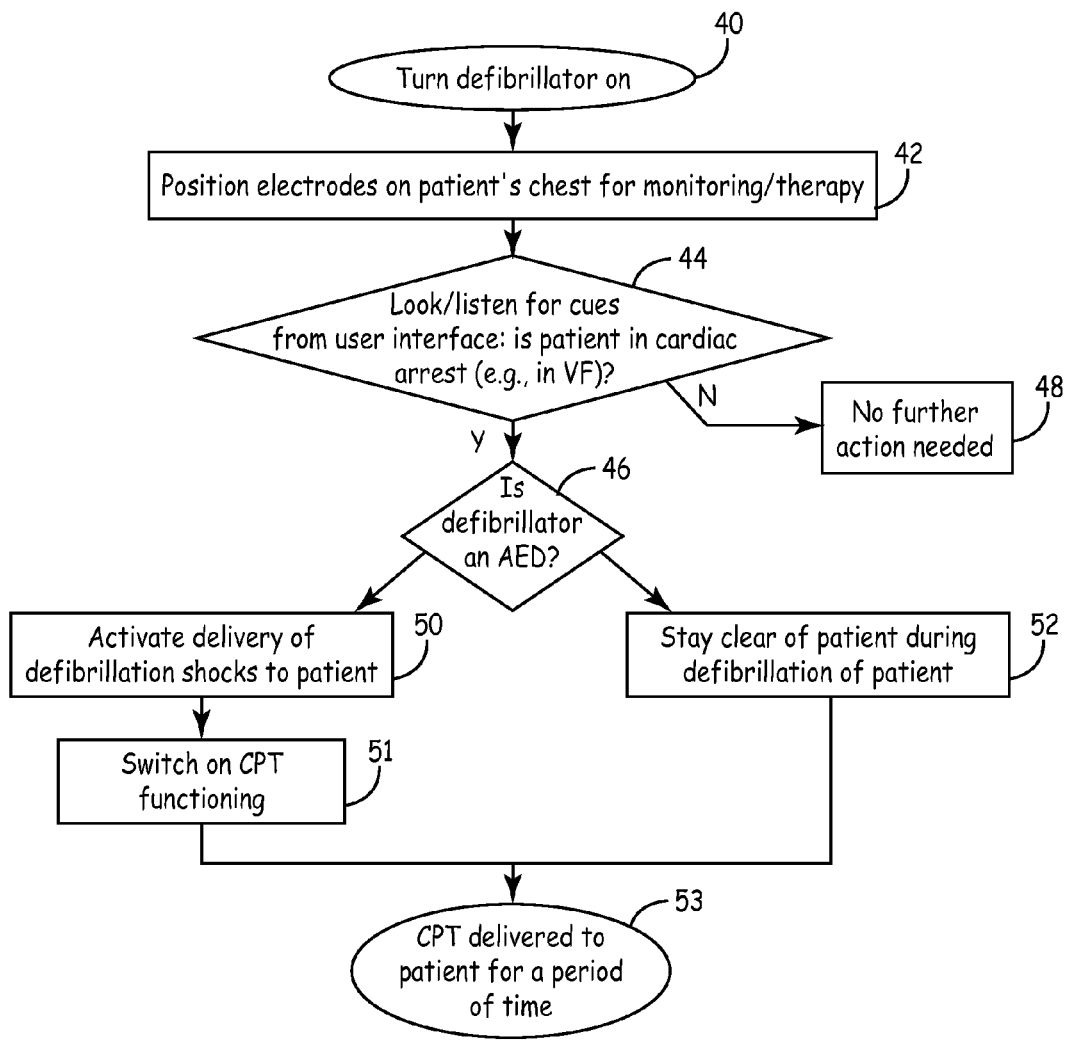
FIG. 2A is a flowchart depicting steps used when automatically delivering following delivery of defibrillation shocks to a patient using the external cardiac medical device of FIG. 1 in accordance with certain embodiments of the invention.

In accordance with the above, FIG. 2A, with reference to the patient 8 and the defibrillator 10 of FIG. 1, is a flowchart depicting steps used in initially delivering CPT following administration of defibrillation shocks in accordance with certain embodiments of the invention. As shown, FIG. 2A has the same initial steps 40-52 already illustrated in FIG. 2 and described above. However, in contrast to that provided in FIG. 2, following delivery of defibrillation shocks to the patient 8 in step 50 (when using a manual external defibrillator) and step 52 (when using an AED), the next series of steps involve the defibrillator immediately being triggered to deliver CPT. In contrast, as described above, an assessment of the patient's cardiac condition is taken (using the patient's cardiac information as a basis) in FIG. 2 prior to administration of CPT to the patient 8.

Accordingly, in the case of the defibrillator 10 being a manual external defibrillator, following delivery of defibrillation shocks to the patient 8 in step 50, a subsequent step involves the operator switching on the CPT functionality, as shown in step 51. In turn, in step 53, CPT is delivered to the patient 8 for a period of time. Conversely, in the case of the defibrillator 10 being an AED, following delivery of defibrillation shocks to the patient in step 52, the defibrillator 10 (via the controller 24) would be configured to automatically deliver CPT to the patient 8 for a period of time as a subsequent action. As such, step 52 leads directly to step 53.

As should be appreciated, FIG. 2A can be partially combined with the steps of FIG. 2. In doing so, the defibrillator 8 can be triggered to deliver CPT for a certain period of time following delivery of defibrillation shocks to the patient, and afterward, the cardiac condition of the patient 8 can be assessed to determine whether the patient reverts to PEA, necessitating further CPT to be delivered to the patient 8. In particular, steps 51 and 53 of FIG. 2A can be positioned between steps 50 and 54 of FIG. 2, while step 53 of FIG. 2A can be positioned between steps 52 and 54' of FIG. 2.

Delivery of CPT: Following a determination that the patient would benefit from CPT, a subsequent concern involves how CPT would be effectively delivered to the patient via the external cardiac medical device, such as the defibrillator 10 of FIG. 1.

As is known, CPT delivery techniques with respect to implantable cardiac medical devices are well documented. For example, detailed discussion regarding delivery of CPT using implantable devices can be found in the above-mentioned '184 U.S. Patent Application Publication, as well as U.S. Pat. Nos. 5,213,098 and 6,738,667 and U.S. Patent Application Pub. Nos. US 2004/0220631, US 2004/0049235, and US 2005/0075675, the disclosures of which are incorporated by reference herein in relevant part. However, as described above, delivery of CPT using external noninvasive devices presents challenges not faced with implantable devices. This is further discussed below.

In CPT, the "coupling interval" is considered to be the time between the first cardiac action potential (e.g., either an intrinsic beat or a driven complex) and the potentiation pulse. The duration of the refractory period of the cardiac cycle varies from patient to patient as well as varying slowly over time in an individual patient, making the selection of a proper coupling interval somewhat problematic. As already alluded to above with respect to the techniques used in determining whether CPT is warranted, in selecting an optimal coupling interval for the patient via any of the techniques described below, the external cardiac medical device, such as the defibrillator 10 of FIG. 1, needs to be equipped for using such techniques accordingly. In particular, this would again involve the controller 24 of the defibrillator 10 being programmed with corresponding instructions. Because one skilled in the art would be familiar with such programming practices as well as other typical manners of implementation within medical devices, such manners of implementation are not discussed in further detail below.

In using an external cardiac medical device, such as the defibrillator 10 of FIG. 1, to define a coupling interval for the patient, certain considerations need to be made. As should be appreciated, one would want the device to use a coupling interval that results in the potentiation pulse being as close to the end of the refractory period as possible so as to provide the most benefit to the patient. However, one would need to be careful in how the coupling interval is defined. For example, one would want to be particularly selective if the coupling interval is based on monitored cardiac information of the patient. This is because such monitored cardiac information would be gathered externally and non-invasively by the device. As is known, there is more room for error in monitoring certain cardiac information with an external device as compared to monitoring the same cardiac information with an implantable device. As such, if the coupling interval is defined in light of monitored cardiac information, the cardiac information needs to be carefully chosen so that monitoring error will be kept low, while still providing a good basis for forecasting an optimal coupling interval for the patient.

In certain embodiments, techniques of defining the coupling interval may not involve using monitored cardiac information as a basis. These techniques would be advantageous as they would be simple to apply and would not require the need to monitor cardiac parameters; however, the techniques may not provide the maximum benefit for the patient all the time. One such technique is to program the controller 24 to automatically use a fixed coupling interval for delivering the potentiation pulses. In certain embodiments, the fixed coupling interval is based on an average coupling interval found to work reasonably well in the majority of the population. In certain embodiments, the fixed coupling interval can remain fixed over time. Alternately, in certain embodiments, the fixed coupling interval can be adjusted over time to other programming coupling intervals. For example, after a defibrillation shock, the coupling interval could be set to a fixed nominal value, as described above. In turn, the controller 24 would be programmed to adjust the coupling interval with respect to the degree that refractory periods normally change following defibrillation therapy.

Another technique is to program the controller 24 so that the coupling interval is made to wander over a range of coupling interval values (which, as similarly described above, are found to work reasonably well in the majority of the population). As should be appreciated, this would increase the likelihood that any given patient would receive optimal treatment some of the time; however, at other times, the treatment may not be optimal. A further technique is to program the controller 24 so that a string of potentiation pulses are delivered every cardiac cycle over an expected period where the optimal point for stimulation may be located. For example, in certain embodiments, the defibrillator 10, via the controller 24, would deliver five pulses, each spaced 40 ms apart, covering a period of about 200 ms. This technique increases the likelihood that one of the pulses would be delivered close to the optimal location.

In certain embodiments, techniques of defining the coupling interval can involve using monitored cardiac information as a basis. For example, one technique is to program the controller 24 to define the coupling interval based on ECG characteristics. While an ECG signal monitored by the external defibrillator 10 (via the electrodes 12, 14) may, at certain times, be adversely affected due to the non-invasive monitoring, using the ECG as a basis for defining the coupling interval would tend to be more effective than the "blind" methods described above. For example, the controller 24 can be programmed to deliver the potentiation pulse at a particular point or segment of the patient's cardiac cycle (using the patient's ECG signal as a guide). As described above, the point or segment chosen would correspond to the typical location in the cardiac cycle where the refractory period is generally found to end in the population. For example, this can involve delivering the potentiation pulse at a fixed percentage of the R-R interval or at a fixed location relative to the T wave. It should be appreciated that certain points or segments in the cardiac cycles of the ECG may be preferable over others depending on the patient's heart rate and the width of the QRST complex. For example, if the patient is being externally paced, then the coupling interval may be set based on the pacing rate rather than a measurement of the R-R interval.

Other techniques can involve programming the controller 24 to actively track the end of the refractory period based on the cardiac information. For example, the refractory period end can be tracked through the sensing of an extrasystole in the cardiac cycle. In turn, a coupling interval can be defined so that subsequent coupled or paired pacing pulses, when delivered, replicate further occurrences of such extrasystole. Alternatively, the coupling interval can be varied so as to continually approximate the optimal coupling interval. In turn, the benefit the patient receives from the potentiation pulses can be optimized. Theoretically, using a coupling interval which terminates as close as possible to the end of the refractory period (without terminating inside the refractory period) will cause maximal potentiation. In certain embodiments, once the end of the refractory period is located, the controller 24 can use a coupling interval just outside of the refractory period (e.g., spaced several tenths of a millisecond outside the refractory period) to guarantee capture and to avoid being in close proximity to the vulnerable zone of the heart's cardiac cycle. As should be appreciated, one may use separate tracking methods for coupling intervals with respect to coupled pacing and paired pacing, as the apparent refractory period may be different for these two cases. In order to actively probe the refractory period, a method must be initially used to detect whether the applied potentiation pulse captured the heart.

For example, one such method can involve programming the controller 24 to mechanically sense the presence of an extrasystole so as to verify capture of the potentiation pulse. In certain embodiments, such sensing can be provided via mechanical sensors (e.g., operatively associated with one or more of the electrodes 12, 14). Another method can involve programming the controller 24 to compare different coupling intervals in an effort to optimize benefit to the patient. For example, the relative strength of mechanical beats from the different coupling intervals can be measured so as to locate the optimal coupling interval. As should be appreciated, in certain embodiments, this method can be used once capture is verified via the first mechanical method provided above. As described herein, an applied pulse within the refractory period would not cause potentiation on the subsequent beat; this beat would appear mechanically weaker than a potentiated beat. A pulse applied farther away from the refractory will also result in lowered potentiation. In certain embodiments, the location of the end of the refractory period is isolated using an algorithm programmed into the controller 24. The algorithm would call for two distinct coupling intervals being used on two separate cardiac cycles. If both coupling intervals result in potentiation, it can be concluded that both were delivered outside the refractory period. However, since both potentiation pulses were delivered according to different coupling intervals, one pulse would likely have resulted in a larger potentiation than the other. In turn, subsequent pulse pairings can be accordingly varied based on the coupling interval that produced the greater potentiation so as continually approximate an optimal coupling interval for the patient.

In another method, instead of mechanically sensing the appearance or relative strength of the potentiated beats as described above, the controller 24 can be programmed to sense mechanical rate to verify whether the applied pulse captures the heart. For example, paired or coupled pacing will generally halve the mechanical rate; in turn, this halving of the rate would confirm adequate capture of the ventricles. A further method can involve the controller 24 being programmed to use an ECG signal to verify whether the applied pulse captures the heart. For example, the end of the refractory period can be identified by adjusting coupling intervals and identifying capture through a surface electrocardiogram measurement. If the applied potentiation pulse is captured by the heart, such would result in an evoked QRS complex or a T-wave. The presence of such elements on an ECG signal would verify the heart being captured.

It has been found that the coupling interval can also be accurately set by assessing changes in the patient's blood flow on a beat-to-beat basis. In certain embodiments, the external device is configured to determine the optimal coupling interval based on the patient's diastolic blood pressure. It should be appreciated that the blood pressure assessment would not need to determine the true value, but only the relative value, of the blood pressure on a beat-to-beat basis. This approach would allow the external device to optimally set the location of the potentiation pulse by dithering the timing of the coupling interval and setting the interval based on the interval which produces the largest subsequent pressure pulse. As should be appreciated, any of the other pulse detection methods (as described above) are suitably applicable to this technique; similarly, pulse oximetry could be also used. As such, the beat-to-beat technique described above should not be limited to only blood pressure assessments.

As should be appreciated, when CPT is delivered to a patient via an AED, its delivery is fully automatic, with the AED determining the need for CPT and setting the coupling interval. Conversely, in a manual defibrillator, in certain embodiments, it is desirable to give the operator certain control of the administration of CPT to the patient. For example, as described above, such control can include giving the operator the ability to activate/deactivate the CPT. Another example of such control can include giving the operator the ability to define or vary the coupling interval used for CPT. With respect to the defibrillator 10 of FIG. 1, such control can be provided to the operator via one or more I/O devices on the user interface 28. As should be appreciated, a trained clinician may have methods of assessing the patient's potentiation and/or the optimal coupling interval that are not available to the defibrillator 10 or may be more accurate than the methods performed by the defibrillator 10.

For example, the trained clinician may take the patient's blood pressure manually or with another device, may have a separate invasive blood pressure monitor, or may have a pulse oximeter with a waveform display so as to optimize the coupling interval. A trained operator may also be able to determine the optimal coupling interval based on changes in the ECG signal. For example, although external ECG monitoring during external stimulation is difficult, a properly trained clinician can generally distinguish between a driven QRS complex and electrical artifact. Likewise, the operator may also be able to determine whether a potentiation pulse has been captured. If so, then the operator can adjust the coupling interval to accordingly adjust the potentiation pulses so that the pulses are captured by the patient's heart. In general, the operator would be able to adjust the coupling interval (thereby, overriding selection of the coupling interval by the defibrillator 10) using any assessment means at his disposal to achieve the optimal results for the patient.

Figure 3:
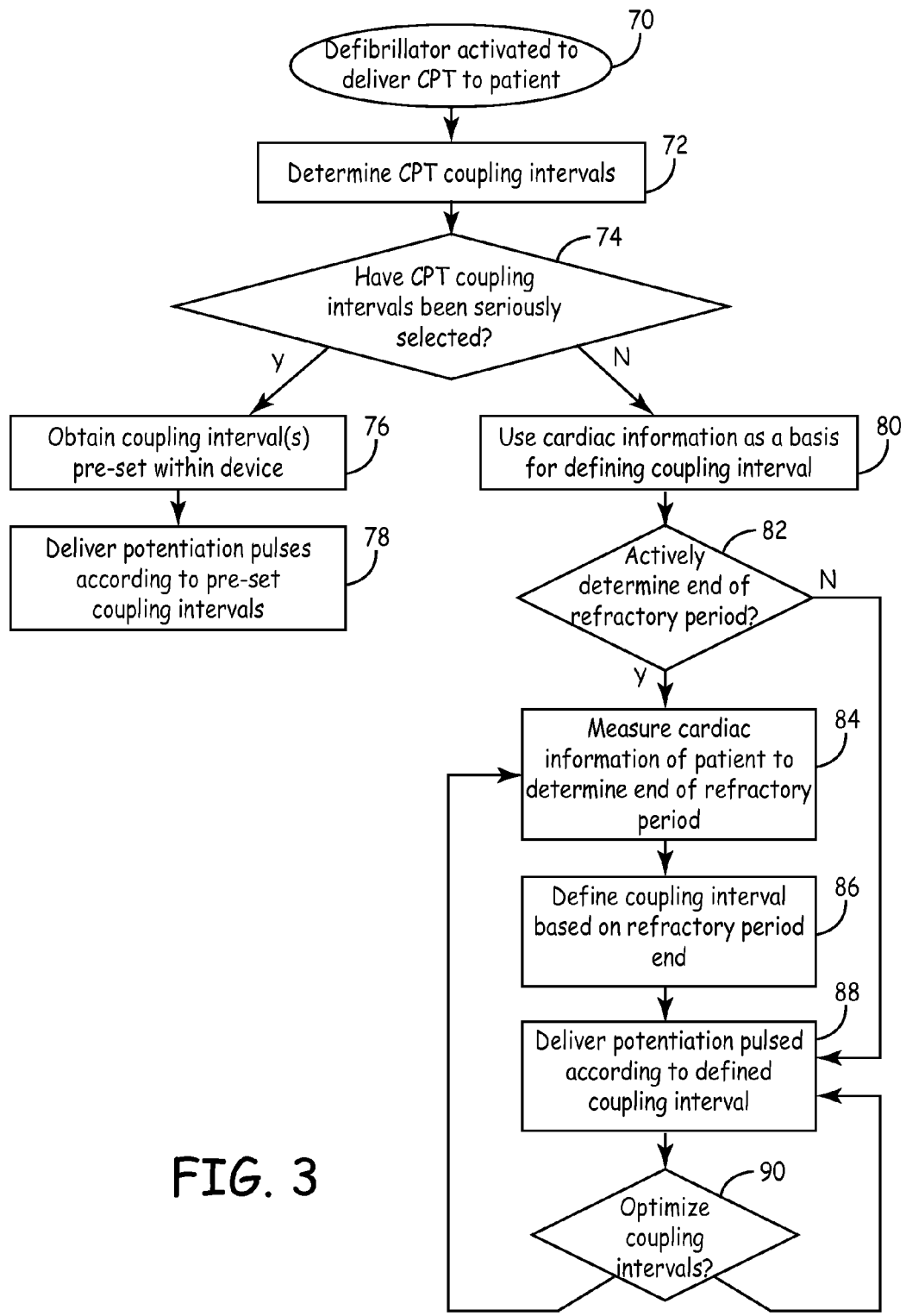
FIG. 3 is a flowchart depicting steps used in administering CPT to a patient using the external cardiac medical device of FIG. 1 in accordance with certain embodiments of the invention.

FIG. 3, with reference to the patient 8 and the defibrillator 10 of FIG. 1, is a flowchart depicting steps used by the external medical device in administering CPT in accordance with certain embodiments of the invention. As should be appreciated, the flowchart of FIG. 3 can be generally viewed as a continuation of the flowchart of FIG. 2, wherein final steps 66 and 68 of flowchart of FIG. 2 and the initial step 70 of flowchart of FIG. 3 involve activating the defibrillator to deliver CPT to the patient 8. In delivering CPT to the patient 8, a coupling interval for the CPT must be initially determined, as referenced in step 72. As described above, one or more coupling intervals are either pre-selected or defined by some means, as represented in step 74. If the one or more coupling intervals are pre-selected, such intervals are programmed/pre-set within the controller 24 of the defibrillator 10 and accordingly collected by the device in step 76. As such, potentiation pulses are delivered to the patient 8 with respect to the pre-set coupling intervals in step 78. Such cases represent the "blind" methods of determining the coupling interval, as described above.

Conversely, the one or more coupling intervals may be defined by other means. For example, in certain embodiments, the coupling intervals are defined based on monitored cardiac information (e.g., cardiac signals and/or hemodynamic parameters) of the patient 8, as shown in step 80. As should be appreciated, the cardiac information can be provided via the defibrillator 10 itself, or alternatively, via actions of the operator (whereby such information would be provided to the defibrillator 10 by the operator via the user interface 28). While not shown in the flowchart of FIG. 3, in certain embodiments, the cardiac information can be provided via the defibrillator 10 as well as via actions of the operator. As described above, one example of such monitored cardiac information can be the ECG signal of the patient.

In certain embodiments, the end of the refractory period can be further and actively tracked, as contemplated in step 82. Tracking the end of the refractory period is a further way to accurately define the coupling period for CPT. If the end of the refractory period is to be tracked, in step 84, the defibrillator 10 would use the same cardiac information as previously used in step 80 or other cardiac information. As described above, the presence/relative strength of an extrasystole or the mechanical rate of the heart can be an accurate indicator as to the end of the refractory period. Accordingly, the coupling interval can be defined based on this in step 86. Subsequently, in step 88, potentiation pulses can be delivered based on the defined coupling interval. As shown, if the end of the refractory period is not actively tracked, steps 84 and 86 can be skipped, with step 82 directly leading to step 88.

As described above, in certain embodiments, the coupling interval can be further optimized so as to maximize the benefit the patient 8 gains from the delivered potentiation pulses. The choice of whether the coupling interval is further optimized is shown in step 90. In certain embodiments, cardiac information is repeatedly monitored to continually track the end of the refractory period so as to define the optimal coupling interval. In turn, step 90 loops back to step 84. Otherwise, step 90 loops back to step 88, where potentiation pulses are again delivered based on the previously defined coupling interval. As described above, FIG. 3 represents the steps an external device can follow in accordance with certain embodiments of the invention. However, as further described above, the coupling interval used by the device can be further modified by the operator, or overridden entirely by the operator who is usually medically trained, e.g., based on cardiac information gathered, independently or otherwise.

Improved Sensing of Cardiac Information: The techniques described above, with respect to (i) determining whether a patient should receive CPT and (ii) actual delivery of CPT, involve analysis of the patient's cardiac information. As described above, this cardiac information is generally provided via sensing means associated with the external cardiac medical device. For example, with reference to the defibrillator 10 of FIG. 1, the electrodes 12, 14 can be used to monitor many of the cardiac information parameters, such as the patient's ECG signal. However, these same electrodes 12, 14 are also used to deliver therapy (e.g., defibrillation shocks or potentiation pulses) to the patient 8. In such a case, there is generally a period of time (generally referred to as "post-shock recovery time") during which the electrodes 12, 14 cannot be used for monitoring purposes because of residual charge stemming from the therapy being administered.

The above dilemma is generally not as problematic with respect to delivery of defibrillation shocks to the patient 8. While delivery of the defibrillation shocks involves creation of a sizeable charge residual on and/or proximate the electrodes 12 and 14, the electrodes 12 and 14 are not used for monitoring cardiac information concurrently during administration of therapy. For example, after receiving defibrillation shocks, the patient 8 typically goes through a period of asystole prior to regaining an organized electrical cardiac rhythm. This brief period of asystole generally allows for much of the residual charge from the defibrillation shock to dissipate. Following this period of asystole, the electrodes 12, 14 can generally be used in monitoring the cardiac information, such as the patient's ECG signal. However, having electrodes with such shared monitoring and therapy-delivering functionality can be problematic when both monitoring and delivery of therapy needs to be provided almost simultaneously, as in the administration of non-invasive pacing or CPT.

As is known, manual external defibrillators equipped for non-invasive pacing are commercially available. In order to enable such defibrillators to monitor and deliver therapy concurrently during such pacing, these defibrillators have been generally equipped with separate electrodes for monitoring and therapy. Conversely, AEDs are typically configured with only a single set of combined monitoring/therapy electrodes because the application of multiple electrode sets has been deemed to be too complicated for AED users. As a result, to date, this solitary AED configuration has precluded application of therapies such as non-invasive pacing in these products. In equipping external cardiac medical devices for delivering CPT, where the devices are only configured to function with one set of electrodes for monitoring and therapy (such as the defibrillator of FIG. 10), the challenge is to address the issue of residual charge remaining on/and or proximate to the electrode following therapy. A number of techniques for achieving such are provided below.

One technique of minimizing the residual charge is to configure the external device to deliver biphasic stimulation pulses, e.g., when delivering CPT. As is known, a typical biphasic pulse rises from zero volts to some prescribed positive voltage, and then switches rapidly to some prescribed negative voltage before returning to zero. Because part of a biphasic pulse is at a positive voltage level and part is at a negative voltage level, the waveform tends to deliver a more balanced charge than a monophasic waveform. A more balanced charge, in turn, would leave less net charge on the interface between the heart and the electrodes, thereby limiting the residual charge on and/or proximate to the electrode following delivery of therapy. In addition, using biphasic pulses can be highly effective in limiting damage to the patient's skin (where the electrodes are positioned) from the current delivered during the therapy. In cases in which the patient is paced as well as potentiated, biphasic pulses again may be used, thereby balancing the charge from each therapy so as to provide each of the stimuli in opposite polarities. In configuring an external cardiac medical device, such as the defibrillator of FIG. 1, to deliver biphasic stimulation pulses, additional circuitry and/or programming would be provided with one or more of the charging circuit 26, the energy storage device 22, and the controller 24. One skilled in the art would appreciate such warranted modifications. As such, further discussion regarding such is not further discussed herein.

Another technique of minimizing the residual charge is to use separate electrodes for monitoring and therapy (as mentioned above) and to place the monitoring electrodes in locations (e.g., right arm, left arm, left leg) that are orthogonal to the therapy current instead of in their normal positions. This approach would minimize the voltage that appears at the monitoring electrodes, and consequently, reduce the offset due to residual charge. Such monitoring electrodes 32 and 34 are exemplarily shown in FIG. 1 with dashed lines, and would generally be smaller in size than the electrodes 12, 14 as their function is limited to monitoring. In certain embodiments, the electrodes 32 and 34 are connected to the switch 16 via conductors 36 and 38, respectively, so that the monitoring and therapy functionality of the defibrillator 10 can be selectively alternated (via the controller 24).

Another method is to minimize the current flow through the monitoring electrodes 32, 34. In so doing, the monitoring electrodes 32 can be made "immune" to the voltage that appears during the therapy. For example, during administration of therapy from the device via the electrodes 12 and 14, the voltage gradient between the monitoring electrodes 32, 34 may cause a small amount of current flow, which polarizes the electrode gel and leaves a residual charge after the current flow of the therapy has stopped. Creating a true "open circuit" condition at the monitoring electrode circuit connections while the therapy current is flowing can stop this current flow. For example, while not shown, a relay (e.g., a mercury wetted reed relay) or a low-leakage FET could be placed in series with the inputs of the electrodes 32, 34, which can be effectively used to open the circuit between the electrodes 32, 34. In addition to eliminating electrode polarization, it can enable rapidly re-initialization of the ECG filters after each pulse. By providing the above benefits, this technique reduces the post-stimulus artifact, making it easier to observe the evoked potential and to properly position the potentiation pulses.

Because AEDs have traditionally been limited to a single set of electrodes, some of the techniques described above would not easily be applied. One method of maintaining the ease of use while providing the functionality of additional electrodes is to utilize large electrode pads that incorporate multiple active areas. With respect to the defibrillator 10 of FIG. 1, in certain embodiments, the pads on the electrodes 12, 14 would be segmented, with a conductive area for therapy (e.g., about 4" in diameter) and a separate conductive area for monitoring (e.g., less than about 1" in diameter). To the user, these pads would be as easy to apply as ordinary monitoring/therapy electrodes, but to the device, they would have many of the advantages of separate monitoring and therapy electrodes. Such method would reduce ECG noise generated during external pacing and would address the problem of common mode rejection, in particular, with respect to AEDs.

Other Aspects Relating to CPT Delivery and its Discontinuance: Certain considerations relating to delivery of CPT using an external cardiac medical device are further described below. One of these considerations relates to exemplary procedures used in administering CPT. Another relates to exemplary procedures used in discontinuing CPT, whether on a temporary or permanent basis. As should be appreciated, the controller within the external device (e.g., the controller 24 within the defibrillator 10 of FIG. 1) can be programmed with corresponding instructions for implementing the above procedures. Once again, as one skilled in the art would be familiar with such programming practices as well as other typical manners of implementation within medical devices, such are not discussed in further detail below.

Procedures for administering CPT may differ when treating different cardiac rhythms of the patient. As should be appreciated, determining which procedure needs to be applied can be a further function of the controller within the external cardiac medical device. For example, with respect to the defibrillator 10 of FIG. 1, the controller 24 is programmed to initially identify the patient's cardiac rhythm (e.g., based on the patient's cardiac information). This is exemplified in the flowchart of FIG. 2 in steps 54-60 or steps 54'-60', where the defibrillator 10 determines whether the patient 8 is in PEA. In turn, once the cardiac rhythm of the patient 8 has been identified, the controller 24 follows a corresponding procedure of administering CPT, either automatically (in the case of an AED) or via some action from the operator (in the case of a manual external defibrillator).

As discussed at length above, one patient cardiac rhythm in which CPT would be beneficial is PEA. If the patient is found to be in PEA or has electromechanical dissociation (EMD), yet has an organized electrical rhythm, pacing is not required. As such, in delivering the CPT, potentiation pulses would be coupled to the intrinsic beat rather than a paced beat. Ideally, the amplitude of the potentiation pulse is adjusted to a level that achieves electrical capture without delivering excessive current. In certain embodiments, this can be done by initially delivering potentiation pulses having higher amplitudes, verifying potentiation benefit from the patient. In turn, the amplitudes of the potentiation pulses are gradually decreased until a pulse amplitude is reached at which the patient still benefits from the therapy. Alternatively, in certain embodiments, potentiation pulses can be initially administered at lower amplitudes and gradually increased until the potentiation benefit is observed.

Another patient cardiac rhythm in which CPT would be beneficial is asystole. For asystole, it is generally desirable to initially apply a string of single pacing pulses and to subsequently watch for signs of electrical capture. In certain embodiments, pacing can be initiated at a maximum current setting (e.g., 200 mA) and, if an evoked potential is subsequently detected, the pacing can be gradually decreased to find the pacing threshold. Alternatively, in certain embodiments, pacing can be initiated at a low setting and increased until capture is achieved. If the pacing pulses are able to achieve electrical capture, then it would be appropriate to look for signs of blood flow; however, if there is no blood flow, then potentiation pulses may be delivered at the same current level as the pacing pulses.

As described above, it is also necessary to consider when to discontinue CPT. During the course of recovery following delivery of therapy, the patient may spontaneously develop the ability to independently maintain adequate blood flow, making CPT unnecessary. However, in cases in which CPT is warranted (e.g., patient having inadequate cardiac output), it would be desirable to determine, after a certain period of time (during which CPT is delivered), whether the patient is able to maintain adequate blood flow independently. Consequently, in certain embodiments, the controller of the external cardiac medical device, e.g., the controller 24 of the defibrillator 10 of FIG. 1 is programmed to periodically interrupt the administration of CPT to reassess the patient's condition.

For example, after 1 to 2 minutes of CPT administration, the CPT can be halted for such reassessment. If the patient's hemodynamics are found to deteriorate following discontinuance of CPT, a conclusion can be made that CPT is still warranted and accordingly provided. In turn, the above procedure (CPT delivered for a certain period, CPT stopped to assess patient's hemodynamics, CPT continued if still warranted) can be continually repeated until the patient 8 is found to regain the ability to independently maintain adequate cardiac output, whereupon CPT can be discontinued, at least temporarily. It should be appreciated that the patient's hemodynamics may later drop off, prompting re-administration of CPT. As such, in certain embodiments, the operator is instructed by the defibrillator 10 (e.g., via the user interface 28) to keep the electrodes 12, 14 in position for a short time after the patient 8 regains ability to independently.

A further application may involve CPR being provided to a patient instead of CPT. In such applications, the monitoring functionality of the CPT therapy can be used in combination with the CPR therapy. As such, CPT reassessment periods can be used in conjunction with the CPR being performed on the patient to not only determine whether the patient is benefiting from the CPR, but also whether the patient has regained the ability to independently maintain adequate cardiac output.

In certain embodiments, the external cardiac medical device is programmed to deliver CPT for a fixed period of time. For example, it is known that most patients experience a period of very low or nonexistent blood flow following delivery of a defibrillation shock. In some cases, the patients may naturally regain normal cardiac output after a certain period of time. In other cases, the patients may regain normal cardiac output as a result of drugs administered to the patient (e.g., epinephrine). In both of the above cases, there is a period of time between delivery of the defibrillation shocks and the natural restoration of the patient's cardiac output. By delivering CPT for a fixed period of time (e.g., at least about 30 seconds), one can bridge the gap in these cases until the patients are found to be able to maintain blood flow on their own.

In certain embodiments, the period of time for CPT delivery is selectively determined by the controller of the external device so as to have optimal benefit to the patient. For example, in certain embodiments, the period of time can be determined in light of the cardiac information monitored from the patient. For example, the period of time for CPT delivery can be determined based on the patient's "down time", with shorter "down times" (e.g., less than 2 minutes) receiving little or no CPT, and longer down times (e.g., greater than 2 minutes) receiving a longer, possibly indefinite, amount.

Figure 4:
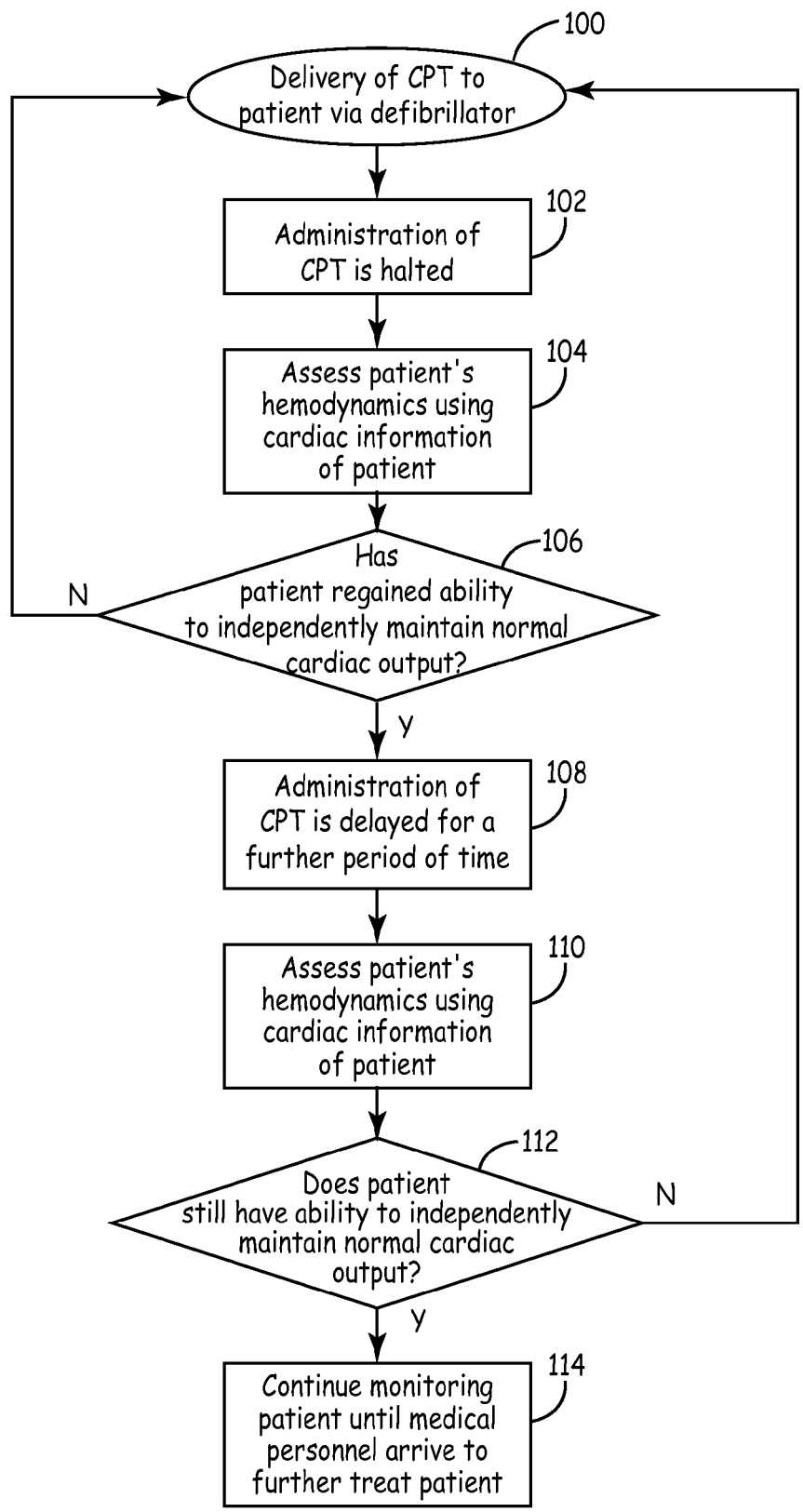
FIG. 4 is a flowchart depicting steps used in discontinuing the administration of CPT from a patient using the external cardiac medical device of FIG. 1 in accordance with certain embodiments of the invention.

FIG. 4, with reference to the patient 8 and the defibrillator 10 of FIG. 1, is a flowchart depicting steps used by the external cardiac medical device regarding discontinuance of CPT in accordance with certain embodiments of the invention. As shown, step 100 involves delivery of CPT to the patient 8 via the defibrillator 10. As should be appreciated, the flowchart of FIG. 4 can be generally viewed as a continuation of the flowchart of FIG. 2, as the final steps 66 and 68 of FIG. 2 involve activating the defibrillator to deliver CPT to the patient 8. In step 102, following a period of time, the defibrillator 10 halts the administration of CPT (via the controller 24). Subsequently, in step 104, the hemodynamics of the patient are assessed using cardiac information monitored from the patient. Accordingly, the cardiac information is processed by the controller 24 to determine whether the patient 8 has regained the ability to independently maintain normal cardiac output in step 106. If the hemodynamics of the patient 8 are found to be deteriorating, step 106 loops back to step 100; otherwise, CPT is delayed for a further period of time in step 108. Following such further period of time, step 110 involves a further assessment of the patient's hemodynamics. In turn, step 112 involves a confirmatory determination that the patient 8 still has the ability to independently maintain normal cardiac output, as previously determined in step 106. If the hemodynamics of the patient 8 are found to be significantly deteriorating, adversely affecting the patient's ability, step 112 loops back to step 100; otherwise, the patient's cardiac output continues to be monitored in step 114 until medical personnel arrive to further treat the patient 8.

It will be appreciated the embodiments of the present invention can take many forms. The true essence and spirit of these embodiments of the invention are defined in the appended claims, and it is not intended the embodiment of the invention presented herein should limit the scope thereof.

The invention claimed is:

1. An external cardiac medical device for delivering cardiac potentiation therapy to a patient, comprising:
   a plurality of electrodes adapted for attachment to external body surfaces of the patient and configured for delivering therapy to the patient;
   a controller electrically connected to the plurality of electrodes; and
   a therapy delivery system electrically connected to the plurality of electrodes, the therapy delivery system configured for delivery of defibrillation shocks to the patient and for delivering electrical stimulation pulses to the patient over a series of cardiac cycles to increase the patient's cardiac output, the controller configured for triggering the delivery of the electrical stimulation pulses following an estimation that cardiac output of the patient is insufficient, the estimation provided via non-invasive assessment of cardiac condition of the patient by one or more of the controller or an operator, the therapy delivery system directed by the controller to deliver the electrical stimulation pulses outside refractory periods of the cardiac cycles;

wherein the non-invasive assessment of the patient's cardiac condition involves consideration of cardiac information of the patient or lack thereof, the cardiac information attained non-invasively, and wherein the cardiac information comprises one or more of cardiac signals and hemodynamic parameters;

wherein the cardiac information comprises one or more measurements supplied by the controller, wherein the one or more measurements comprise one or more of ventricular fibrillation duration and one or more patient pulse detection measurements; and wherein the ventricular fibrillation duration comprises a time period beginning at activation of the external cardiac medical device and ending at delivery of the defibrillation shocks, and wherein a measured time period greater than two minutes comprises a trigger for the delivery of the electrical stimulation pulses.

2. An external cardiac medical device according to claim 1, wherein the therapy delivery system is further configured for delivering pacing pulses to the patient and, the delivery of the electrical stimulation pulses comprises delivery of each of the electrical stimulation pulses paired with an intrinsic event or a paced event within the series of cardiac cycles.

3. An external cardiac medical device according to claim 2, wherein the cardiac information further comprises one or more measurements supplied by the operator, wherein the one or more measurements comprise one or more of pulse and blood pressure.

4. An external cardiac medical device according to claim 2, wherein the one or more pulse detection measurements further comprise measurement of QRS complexes of an ECG signal, wherein a succession of wide QRS complexes comprises a trigger for the delivery of the electrical stimulation pulses.

5. An external cardiac medical device according to claim 2, wherein the controller is configured for interpreting the cardiac information in order to direct the therapy delivery system to deliver the electrical stimulation pulses outside the refractory periods of the cardiac cycles.

6. An external cardiac medical device according to claim 2, wherein the plurality of electrodes comprises a single pair of electrodes, the single pair of electrodes having both therapy and monitoring functionality.

7. An external cardiac medical device according to claim 6, wherein the electrical stimulation pulses comprise biphasic pulses.

8. An external cardiac medical device according to claim 6, wherein the electrodes of the single pair each have segmented pads, wherein each segmented pad has at least one conductive area for therapy and at least one conductive area for monitoring.

9. An external cardiac medical device according to claim 1, wherein the electrical stimulation pulses comprise a first string of pulses either having gradually increasing or gradually decreasing amplitudes followed by a second string of pulses having an optimal amplitude, the optimal pulse amplitude benefiting the patient yet without delivering excessive current to the patient.

10. An external cardiac medical device for delivering cardiac potentiation therapy to a patient, comprising:

a plurality of electrodes adapted for attachment to external body surfaces of the patient and configured for delivering therapy to the patient;

a controller electrically connected to the plurality of electrodes; and a therapy delivery system electrically connected to the plurality of electrodes, the therapy delivery system configured for delivery of defibrillation shocks to the patient and for delivering electrical stimulation pulses to the patient over a series of cardiac cycles to increase the patient's cardiac output, the controller configured for triggering the delivery of the electrical stimulation pulses following delivery of one or more defibrillation shocks to the patient and an estimation that cardiac output of the patient is insufficient, the therapy delivery system directed by the controller to deliver the electrical stimulation pulses outside refractory periods of the cardiac cycles;

wherein the estimation comprises measurement of ventricular fibrillation duration and wherein the ventricular fibrillation duration comprises a measured time period beginning at activation of the external cardiac medical device and ending at delivery of the defibrillation shocks.

11. A device according to claim 10 wherein the measured time period is greater than two minutes.

12. A device according to claim 11 wherein the therapy delivery system is further configured for delivering pacing pulses to the patient and, the delivery of the electrical stimulation pulses comprises delivery of each of the electrical stimulation pulses paired with an intrinsic event or a paced event within the series of cardiac cycles.

13. A device for delivering cardiac potentiation therapy to a patient, comprising:

a plurality of electrodes adapted for attachment to the body of the patient and configured for delivering therapy to the patient;

a controller electrically connected to the plurality of electrodes; and a therapy delivery system electrically connected to the plurality of electrodes, the therapy delivery system configured for delivery of defibrillation shocks to the patient and for delivering electrical stimulation pulses to the patient over a series of cardiac cycles to increase the patient's cardiac output, the controller configured for triggering the delivery of the electrical stimulation pulses following delivery of one or more defibrillation shocks to the patient and an estimation that cardiac output of the patient is insufficient, the therapy delivery system directed by the controller to deliver the electrical stimulation pulses outside refractory periods of the cardiac cycles;

wherein the estimation comprises measurement of ventricular fibrillation duration and wherein the ventricular fibrillation duration comprises a measured time period beginning at activation of the device and ending at delivery of the defibrillation shocks.

14. A device according to claim 13 wherein the therapy delivery system is further configured for delivering pacing pulses to the patient and, the delivery of the electrical stimulation pulses comprises delivery of each of the electrical stimulation pulses paired with an intrinsic event or a paced event within the series of cardiac cycles.

* * * * *